United States Patent [19]
Fujio et al.

[11] Patent Number: 5,402,788
[45] Date of Patent: Apr. 4, 1995

[54] DIAGNOSTIC SYSTEM USING NUCLEAR MAGNETIC RESONANCE PHENOMENON

[75] Inventors: Koji Fujio, Tokyo; Masakazu Gotanda, Kanagawa; Tatsuya Yamaguchi, Tokyo; Shuichi Takayama, Tokyo; Takashi Tsukaya, Tokyo; Toshihiko Hagiwara, Tokyo; Koichi Matsui, Tokyo; Hiroki Hibino, Tokyo; Keiichi Hiyama, Tokyo; Koichi Shimizu, Tokyo; Kenji Yoshino, Tokyo; Masaaki Hayashi, Tokyo, all of Japan

[73] Assignee: Olympus Optical Co., Ltd., Tokyo, Japan

[21] Appl. No.: 80,224

[22] Filed: Jun. 21, 1993

[30] Foreign Application Priority Data

Jun. 25, 1992 [JP] Japan .................. 4-167627
Oct. 9, 1992 [JP] Japan .................. 4-271850
Feb. 17, 1993 [JP] Japan .................. 5-028088

[51] Int. Cl.$^6$ ........................... A61B 5/055
[52] U.S. Cl. ................... 128/653.2; 128/6; 128/4
[58] Field of Search .......... 128/653.2, 653.5, 656, 128/657, 658, 4, 6; 324/322

[56] References Cited

U.S. PATENT DOCUMENTS

| | | | |
|---|---|---|---|
| 4,572,198 | 2/1986 | Codrington | 128/653.2 |
| 4,672,972 | 6/1987 | Berke | 128/653.5 |
| 4,737,712 | 4/1988 | Stormont et al. | |
| 4,843,323 | 6/1989 | Encellaz et al. | |
| 4,932,411 | 6/1990 | Fritschy et al. | 128/643.5 X |
| 4,950,993 | 8/1990 | Encellaz et al. | |
| 4,951,009 | 8/1990 | Collins | |
| 4,960,106 | 10/1990 | Kubokawa et al. | 128/653.5 X |
| 5,035,231 | 7/1991 | Kubokawa et al. | |
| 5,050,607 | 9/1991 | Bradley et al. | |
| 5,143,068 | 9/1992 | Muennemann et al. | |
| 5,170,789 | 12/1992 | Narayan et al. | 128/653.5 |
| 5,188,111 | 2/1993 | Yates et al. | 128/4 X |
| 5,265,610 | 11/1993 | Darrow et al. | 128/653.2 X |
| 5,271,400 | 12/1993 | Dumoulin et al. | 128/653.2 |
| 5,348,010 | 9/1994 | Schnall et al. | 128/653.2 |

FOREIGN PATENT DOCUMENTS

| | | |
|---|---|---|
| 0230168 | 7/1987 | European Pat. Off. |
| 0385367 | 9/1990 | European Pat. Off. |
| 2-277440 | 11/1990 | Japan |
| 3-5174 | 1/1991 | Japan |
| 3-212262 | 9/1991 | Japan |
| 4129533 | 4/1992 | Japan ............... 128/653.2 |
| 3005706 | 4/1993 | WIPO ............... 128/653.5 |

*Primary Examiner*—Lee S. Cohen
*Assistant Examiner*—Brian L. Casler
*Attorney, Agent, or Firm*—Frishauf, Holtz, Goodman & Woodward

[57] ABSTRACT

A diagnostic system using a nuclear magnetic resonance phenomenon comprises an external magnetic field generator, provided externally, for generating a magnetic field in a living body, a thin diameter member capable of being inserted into a body cavity and having flexibility, a high frequency coil, provided at a top end of the thin diameter member, for transmitting and receiving a high frequency, a nuclear magnetic resonance signal measuring device for receiving a nuclear magnetic resonance signal from the living body, and a transformer, provided between the high frequency coil and the nuclear magnetic resonance signal measuring device, for electrically isolating and separating the high frequency coil from the nuclear magnetic resonance signal measuring device in a manner such that the nuclear magnetic resonance signal is transmittable between the high frequency coil and the nuclear magnetic resonance signal measuring device.

17 Claims, 11 Drawing Sheets

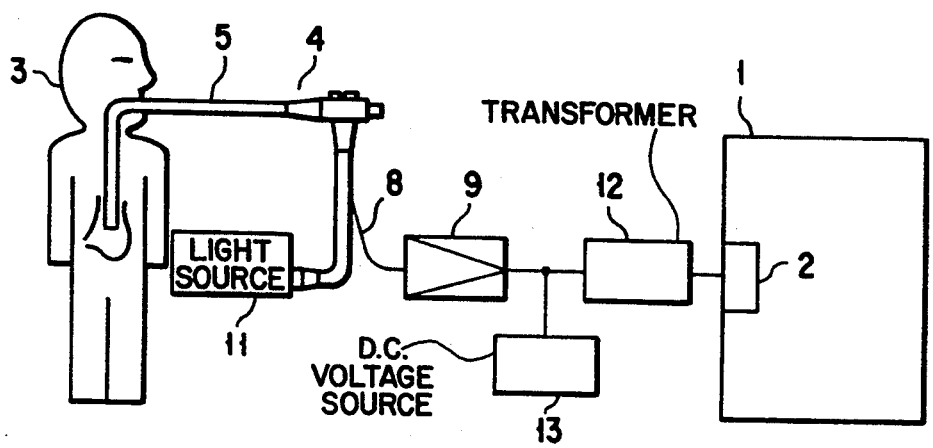
F I G. 2
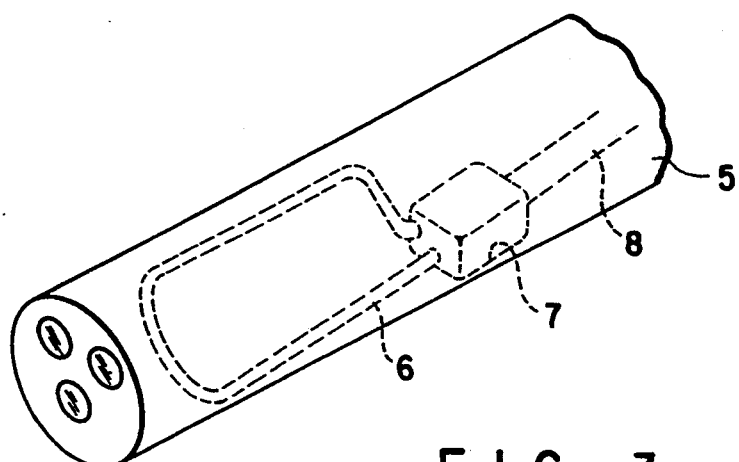
F I G. 3

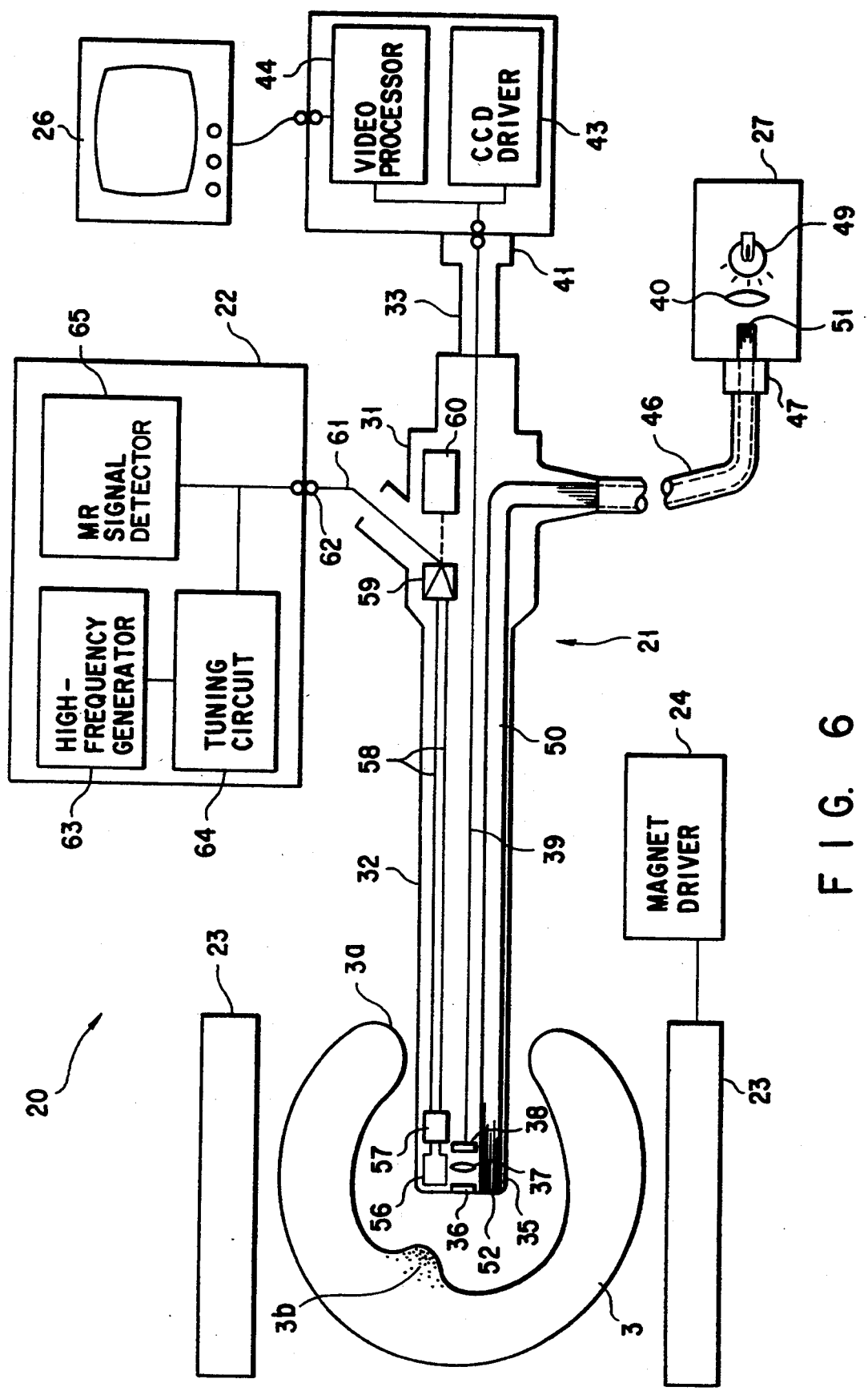
F I G. 6

DIAGNOSTIC SYSTEM USING NUCLEAR MAGNETIC RESONANCE PHENOMENON

BACKGROUND OF THE INVENTION

1. Field of the Invention

The present invention relates to a diagnostic system using a nuclear magnetic resonance phenomenon wherein a nuclear magnetic resonance signal receiving coil is inserted into a human body and a nuclear magnetic resonance image is formed.

2. Description of the Related Art

Conventionally, in the detection and diagnosis of a surface of a digestive organ of a human body, particularly to epidermal cancer generated in stomach walls or an upper layer of the intestinal canal, the general method was that the generated portion was detected by an endoscope or an X-ray diagnosis, and tissues of a living body of the generated portion was picked up, and was determined whether it is malignant or not.

However, in such a conventional method, since the sampling portion became a relatively wide range, there were problems in that the result of the diagnosis was not able to be determined, and it took much time to pick up the tissues of the living body, and the human body was damaged.

On the other hand, there has recently been widely used a non-attacking diagnosing method for a human body which utilizes a nuclear-magnetic resonance phenomenon (the nuclear-magnetic resonance being hereinafter referred to as the "MR"). With a magnetic resonance imaging device (the magnetic resonance imaging being hereinafter referred to as the "MRI"), a human body is placed in a static magnetic field, and a predetermined high frequency magnetic field is applied to the human body to excite nuclei having spins of the tissues in the body cavity of the human body. MR signals having a predetermined frequency produced until the excited nuclei return to the original positions are detected and processed by a computer to obtain vertical cross-sectional images of the body cavity of the human body.

The cross-sectional image obtained by the MRI device is extremely effective for diagnosis such as distinction between abnormal cells (such as cancer cells) and normal cells. It is known that MR signals from cancer tissues and normal tissues are generated at different relaxation time. Therefore, it is possible to diagnose whether the living tissues to be examined are cancer cells or not by imaging a difference between the MR signals in density based on the relaxation time.

Fine and accurate images must be obtained to diagnose diseases of the digestive system such as a tubular viscus and particularly to find the depths of its affected portions. However, since the MR signal receiving body coil is provided externally of a patient's body with the conventional apparatus, it is difficult to obtain fine and accurate cross sectional images of depth portions of the tubular viscus of the patient. For example, with a conventional system, a surface coil for receiving MR signals is placed on the abdomen of a patient and receives MR signals to diagnose the stomach walls. However, the signal-to-noise ratio (hereinafter referred to as the "SN ratio") is too low to obtain images sufficient for required diagnosis.

In order to overcome this problem, there has been proposed an insertion apparatus such as an endoscope or a probe, which is provided, on the distal end of an insertion section inserted in the body of a patient, with an MR signal receiving high frequency coil, for detecting MR signals, as disclosed in Published Examined Japanese Patent Application No. 3-5174 and Published Unexamined Patent Application No. 2-277440. With them, a coil inserted in the patient's body receives MR signals and provides fine and accurate images having a good SN ratio. Thus, fine and accurate images can be obtained for diagnosing the depths of affected portions of tubular viscus.

However, the conventional nuclear magnetic resonance diagnostic apparatus is structured as shown in FIG. 1. More specifically, reference numeral 1 is an MRI apparatus, which comprises an MR signal measuring device 2. On the other hand, in the inside of a top end portion of an insertion section 5 of an endoscope 4 inserted to the body cavity of a patient 3, a high frequency coil, which is an MR antenna for receiving an MR signal.

The high frequency coil is connected to a cable 8 through a matching circuit arranged in the top end portion 5 of the endoscope 4. The matching circuit matches impedance between the high frequency coil and the cable 8, and the cable 8 transmits the MR signal received by the high frequency coil. The cable 8 is connected to the MR signal measuring device 2 through a front amplifier 9, and a universal cord 10 of the endoscope is connected to a light power source device 11.

In such a conventional nuclear magnetic resonance diagnostic apparatus, the high frequency coil provided in the insertion section 5 of the endoscope 4 is not electrically insulated/separated from the nuclear magnetic resonance signal measuring device 2. In other words, in the endoscope with the built-in high frequency coil or the probe, the portion including the matching circuit and the cable 8 is in an electrically conductive live state.

In the conventional endoscope 4 or the probe, if the outer sheath of the insertion portion 5 is broken and the high frequency coil 6 and the mucous membrane of the living body is in a conductive state, there is fear that leakage current a will flow to the patient 3.

SUMMARY OF THE INVENTION

The present invention has been made in consideration of the above-mentioned problems, and an object of the present invention is to provide a nuclear magnetic resonance diagnostic system wherein safety, in view of the patient leakage current, can be ensured with high reliability even if a high frequency coil is provided in an insertion section which is inserted into a human cavity.

According to the present invention, there is provided a diagnostic system using a nuclear magnetic resonance phenomenon comprising an external magnetic field generator, provided externally of a human body, for generating a magnetic field in a living body, a thin diameter member capable of being inserted into body cavity and having flexibility, a high frequency coil, provided at a top end of the thin diameter member, for transmitting and receiving a high frequency signal, a nuclear magnetic resonance signal measuring device for receiving a nuclear magnetic resonance signal from the living body, and isolating and separating means, provided between the high frequency coil and the nuclear magnetic resonance signal measuring device, for electrically isolating and separating the high frequency coil from the nuclear magnetic resonance signal measuring device in a manner such that the nuclear magnetic resonance signal is transmittable between the high frequency coil and the nuclear magnetic resonance signal measuring device.

An external magnetic field generator receives a nuclear magnetic resonance signal from, e.g., an excited hydrogen atom by the high frequency coil provided in the top end portion of the insertion section inserted into the body cavity of the patient. The nuclear magnetic resonance signal received by the high frequency coil is transmitted to the nuclear magnetic resonance signal measuring means of the external magnetic field generator separated by the separating means, and such received, transmitted and insulated unclear magnetic resonance signal is processed by the external magnetic field generator, and a nuclear magnetic resonance signal image can be formed.

According to the diagnostic system of the present invention, safety of the patient in view of electrical leakage can be ensured without deteriorating the quality of the MRI image, and extremely fine and accurate MR image-diagnosis can be performed in a safe state of MR diagnosis.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 is a schematic view of an MRI apparatus for diagnostic system according to the present invention;

FIG. 3 is a schematic perspective view of a portion where an endoscope using the MRI apparatus of FIG. 1 is inserted;

FIG. 6 is a schematic view showing a state that the endoscope using the diagnosis system of the present invention, an MR signal measuring device, and a camera control unit are connected;

DETAILED DESCRIPTION OF THE PREFERRED EMBODIMENTS

Figure 1:
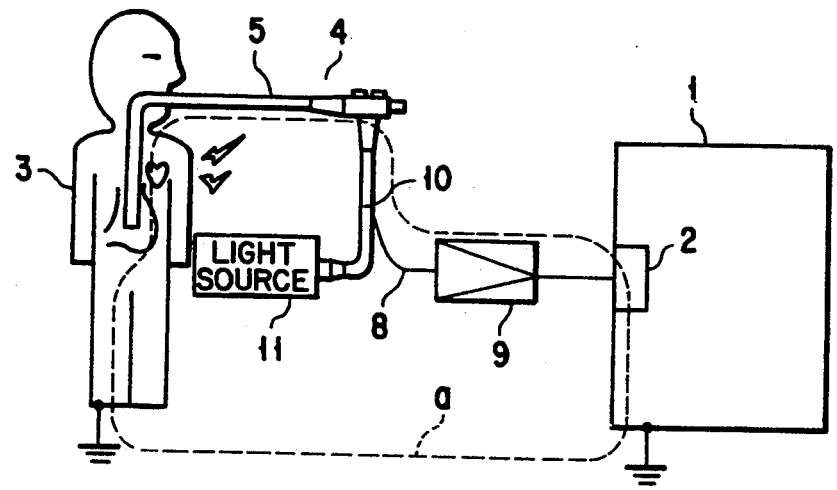
FIG. 1 is a schematic structural view of a conventional MRI apparatus.

Embodiments of the present invention will be explained with reference to the drawings. It is noted that the same reference numerals designate the same portions through all figures.

FIGS. 2 and 3 show a first embodiment of a diagnostic system using a unclear magnetic resonance phenomenon. An MR signal receiver of an MRI apparatus or an MR signal measuring device 2 is connected to a front-stage amplifier 9 through a separating means 12. A high frequency coil 6, which is a MR antenna for receiving an MR signal, is provided in a top end portion of an insertion portion 5 of an endoscope 4, which is inserted into a cavity of a living body 3 of a patient to be examined. The high frequency coil 6 and the front-stage amplifier 9 are connected to each other via a cable 8.

The high frequency coil 6 is connected to the cable 8 through matching means or circuit 7. The matching circuit 7 matches impedance of the high frequency coil 6 and cable 8. The cable 8 transmits the MR signal received by the high frequency coil 6. The cable 8 is connected to the MR signal measuring device 2 through the front amplifier 9, and a universal cord 10 of the endoscope 4 is connected to a light source device 11.

Separating means 12 is formed of, e.g., a transformer. If a side, which is connected to the MR signal measuring device 2, is a primary side and a side, which is connected to the high frequency coil 6, is a secondary side, a stabilizing d.c. voltage source 13 for supplying a bias voltage to the front-stage amplifier 9, e.g., a battery to which a voltage stabilizing circuit is attached is connected to the secondary side.

According to the above-structured nuclear magnetic resonance diagnostic apparatus, the MRI apparatus 1 receives an MR signal sent from, e.g., a hydrogen atom by use of the high frequency coil 6 provided at the top end portion of the insertion portion 5 of the endoscope inserted into the cavity of the living body 3 of a patient.

The MR signal received by the high frequency coil 6 is transmitted to the cable 8, whose impedance is matched by the matching circuit 7, and the received MR signal is amplified by the front-stage amplifier 9 using the stabilizing d.c. voltage source 13 as a power source.

The MR signal measuring device 2 of the MRI apparatus 1 is electrically isolated/separated from the high frequency coil 6, which is connected to the cable 8, by separating means 12 such as a transformer, and the MR signal is transmitted to the MR signal measuring device 2 of the MRI apparatus 1. The MR signal, which is received by the MR signal measuring device 2, and transmitted, and isolated, is processed by the MRI apparatus 1, and an MR signal image is formed.

According to the above embodiment, a patient circuit forms the high frequency coil 6, the matching circuit 7, and the cable 8 for transmitting the signal, which are isolated/separated from the MRI apparatus 1.

Due to this, it is possible to control a patient leakage current, which flows to an earth (ground potential) from the MRI apparatus 1 via the high frequency coil 6 and the patient 3. Therefore, the leakage current to a patient mounting portion can be controlled to be lower than an allowable value, which is defined by IEC 601-1. Moreover, in the case that the high frequency coil 6 is inserted to the living body of the patient and the MR image diagnosis is performed, it is possible to ensure safety in view of the patient leakage current.

Figure 4:
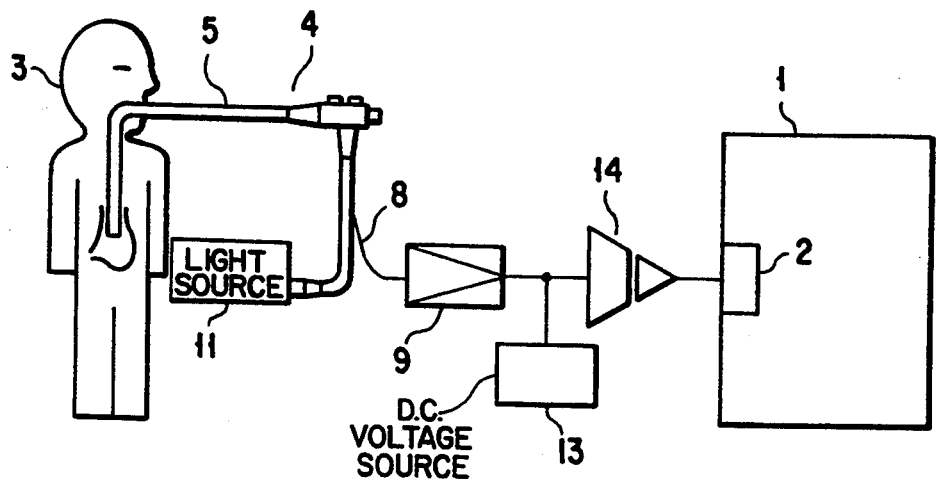
FIG. 4 is a view of an MRI apparatus according to the other embodiment of the present invention similar to FIG. 2.

FIG. 4 is a second embodiment of the present invention. Similar to the first embodiment, the front-stage amplifier 9 is connected to the cable 8, which is connected to the high frequency coil 6. The front-stage amplifier 9 is connected to the MR signal measuring device 2 of the MRI apparatus 1 through an isolation amplifier 14 serving as isolating/separating means for isolating/separating the signal and amplifying the signal.

In a case that the isolation amplifier 14 is an amplifier, which does not pass the direct current, the stabilizing d.c. voltage source 13, which supplies the voltage to the front-stage amplifier 9 and the isolation amplifier 14, is connected to the front-stage amplifier 9 and the isolation amplifier 14 as shown in FIG. 4.

Figure 5:
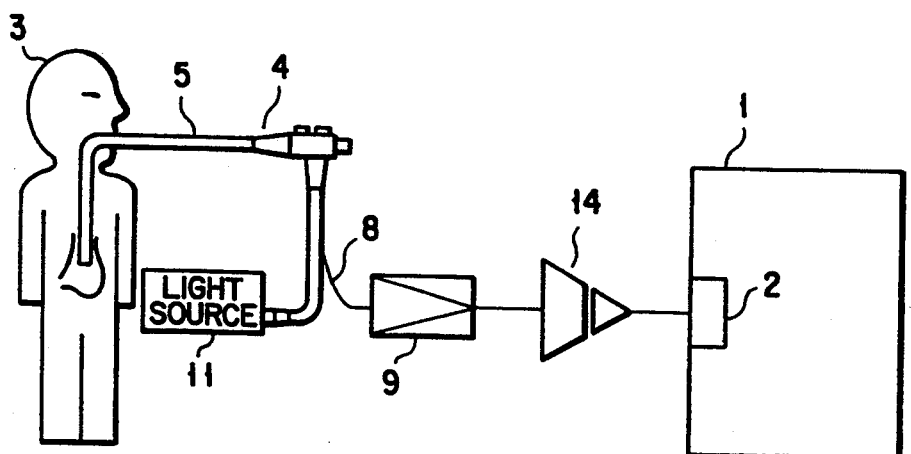
FIG. 5 is a view of an MRI apparatus according to a modification of the present invention similar to FIG. 2.

If a case that the isolation amplifier 14 is an amplifier which passes the direct current, the direct current, which is isolated from the surrounding earth (ground potential), is supplied to the front-stage amplifier 9 and the isolation amplifier 14 from the MRI apparatus 1, so that no connection of the stabilizing d.c. voltage source 13 is needed as shown in a modification of FIG. 5.

According to the above-structured nuclear magnetic resonance diagnosis apparatus, the MR signal is received by the high frequency coil 6 formed at the top end portion of the insertion portion 5 of the endoscope 4. The received signal is amplified by the front stage amplifier 9, and isolated and separated by the isolation amplifier 14. Thereafter, the signal is inputted to the MR signal measuring device 2 of the MRI apparatus 1.

Therefore, similar to the first embodiment, the patient circuit, which is inserted to the body of the patient 3, can be electrically isolated, and the safety of the patient 3 can be ensured in view of the leakage current. Moreover, since the signal can be amplified in the isolation and separation, an SN ratio of the diagnostic image can be improved.

FIGS. 6 to 9 are embodiments showing a diagnostic system in which an endoscope with a built-in high frequency antenna can be selectively connected to an arbitrary MR measuring device having various circuit characteristics.

Figure 7:
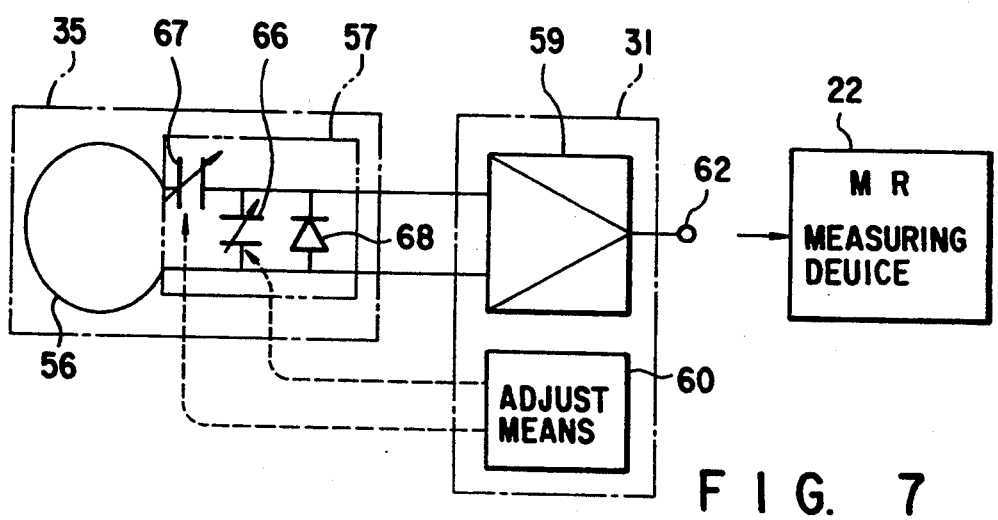
FIG. 7 is a schematic circuit diagram of the endoscope of FIG. 6.

FIG. 6 is a general view of the above diagnostic system, and FIG. 7 is a circuit diagram of matching means.

As shown in FIG. 6, a diagnostic system 20 comprises an MR endoscope 21, an MR detecting device or an MR measuring device 22, a magnet 23, a magnet driver 24, a camera control unit (CCU) 25, a monitor 26, and a light source device 27.

The endoscope 21 forms a long and thin inserting portion 32, which is stretched to the forward portion from a handy controller 31, and a universal cord 33, which is extended from the back portion of the handy controller 31. An objective optical system 37, which image-forms an incident light, which is inputted through a cover glass 36, on a focal plane, is arranged on a top end portion 35 of the insertion portion 32. An image device 38 such as a CCD is arranged on the focal plane of the objective optical system 37. A signal line 39 extends in the universal cord 33 through the top end portion 35, the insertion portion 32, and the handy controller 31. The universal cord 33 has a connector 41 in its end portion, and is connected to the CCU 25 by the connector 41.

The CCU 25 comprises a CCD driver 43 and a video processor 44. The image device 38 is driven by a CCD driving signal outputted from the CCD driving circuit 43. An image signal outputted from the image device 38 is sent to the video processor 44 through the signal line 39b and converted to a standard TV signal for a monitor display by the video processor 44, and outputted to the monitor 26.

Moreover, a light guide cord 46 is extended from the side surface of the controller 31 of the endoscope 21, and is connected to the light source device 27 by a connector 47 provided at one end of the light guide cord 46. The light source device 27 supplies electrical power to a light source 49 by a light source driver (not shown), and emits the light source 49. Light supplied from the light source 49 is focused on the focal plane by a capacitor lens 40. An end surface 51 of a light guide 50, which is extended in the insertion portion 32 of the endoscope 21 and the inside of the light guide cord 46, is arranged on the focal plane. Thereby, light emitted from the light source 49 is passed through the end surface 51, and transmitted into the light guide 50. Light transmitted into the light guide 50 is emitted from an emission end surface 52 arranged on the top end portion 35, and an object to be examined in the body cavity can be lightened.

In the top end portion 35 of the endoscope 21, there are provided a loop antenna 56, which is an MR antenna, and a matching circuit 57 connected to the loop antenna 56. The loop antenna 56 can be made of non-magnetic wire material having elasticity such as a wire in which a copper wire or spring material is plated with gold, or a wire in which a superelastic alloy and a copper wire are twisted. The loop-shape can be obtained by elasticity of the wire material. A signal line 58 is extended to the handy controller 31 from the matching circuit 57 through the insertion portion 32.

The handy controller 31 has a pre-amplifier 59 and adjusting means for adjusting the matching circuit 57. The pre-amplifier 59 is connected to the adjusting circuit 57 through the signal line 58. Moreover, a signal line 61 is extended to the outer portion of the endoscope 21 from the pre-amplifier 59, and connected to the MR measuring device 22 by an electrical contact 62 provided at the top end.

The MR measuring device 22 comprises a high frequency generator 63, a tuning circuit 64, and an MR signal detector 65. The tuning circuit 64 tunes a high frequency, which is generated by the high frequency generator 63, to a resonance frequency corresponding to the type of an object to be measured. Then, the tuned high frequency is transmitted to the loop antenna through the matching circuit 57, and a high frequency magnetic field is outputted to the living body from the loop antenna 56. The loop antenna 56 serves as both a transmitter and a receiver and the MR signal sent from the living body is received by the loop antenna 56 and the MR signal is inputted to an MR signal detector 65 through the matching circuit 57, and the high frequency magnetic field is outputted to the living body from the loop antenna 56. The loop antenna 56 serves as both a transmitter and a receiver. The MR signal sent from the living body is received by the loop antenna 56, and inputted to the MR signal detector 65 through the matching circuit 57 and the pre-amplifier 59. Then, data of such as a relaxation time can be obtained by the MR signal detector 65.

FIG. 7 shows a circuit of the MR measuring section including the matching circuit 57. The matching circuit 57, which is connected to the loop antenna 56, has a variable capacitor 66, which is connected to the antenna 56 in parallel, and a variable capacitor 67, which is connected to the antenna 56 in series. By these capacitors 66 and 67, the impedance between the side of the antenna 56 and the side of the high frequency generator 63, which the MR measuring device 22 has, is matched. As mentioned above, these capacitors 66 and 67 are variable and the capacities of the capacitors 66 and 67 are adjusted by adjusting means 60, which is provided in the controller 31, the impedance to the connected MR measuring device 22 is matched. Moreover, a diode 68 is connected to the loop antenna in parallel.

The body 3 of the patient to be examined is mounted on a bed (not shown), and a static magnetic field is applied thereto by the magnet 23 driven by the magnet driver 24.

In the above embodiment, the loop antenna was used as an MR antenna. However, the present invention is not limited to the MR antenna, and an antenna, which is generally used as an MR endoscope, such as a coil antenna, may be used.

The operation of the above-structured diagnostic system will be explained as follows:

As shown in FIG. 6, the living body 3, which is an object to be examined, is mounted on the bed (not shown), and the static magnetic field is applied thereto by the magnet 23. Under this condition, the insertion unit 32 of the MR endoscope 21 having the loop antenna for MR measurement is inserted into a body cavity 3a of the person to be examined. An illumination light is supplied from the light source device 27 and an image signal, which is obtained from the objective optical system 37 through the image device 38, is examined by the monitor 26, and the loop antenna 56 of the top end portion 35 is arranged in the vicinity of the object to be examined such as an abnormal portion 3b.

Next, a high frequency is generated by the MR measuring device 22, and a high frequency magnetic field is transmitted to the abnormal portion 3b from the antenna 56. It is noted that the direction of the high frequency is preferably perpendicular to the direction of the static magnetic field. The MR signal sent from the abnormal portion 3b is received by the antenna 56 and measured by the MR signal detector 65, thereby making it possible to determine a physiological change of the abnormal portion 3b, e.g., whether or not the abnormal portion 3b is a cancer.

At this time, the loop antenna 56 of the top end portion 35 and the MR measuring device 22 are matched by the matching circuit 57, which is suitably adjusted by adjusting means 60. However, for connecting a different MR measuring device to MR endoscope 21, the matching circuit 57 must be further adjusted. In this case, adjusting means shown in FIG. 7 is adjusted by hand to control the capacities of two variable capacitors 66 and 67 of the matching circuit 57, so that an impedance matching state, which is suitable for the different MR measuring device, can be obtained, and the different MR measuring device can be connected to MR endoscope 21.

According to the embodiment of the diagnostic system shown in FIGS. 6 and 7, the circuit characteristic, which is suitable for the MR measuring device 22 to be connected, can be obtained by the matching circuit 57, which is adjustably provided in the MR endoscope 21, and adjusting means 60 for adjusting the matching circuit. Thereby, a plurality of MR measuring devices having various circuit characteristics can be used. Moreover, since adjusting means 60 is provided in the handy controller 31, the control operation can be easily performed.

Figures 8, 9:
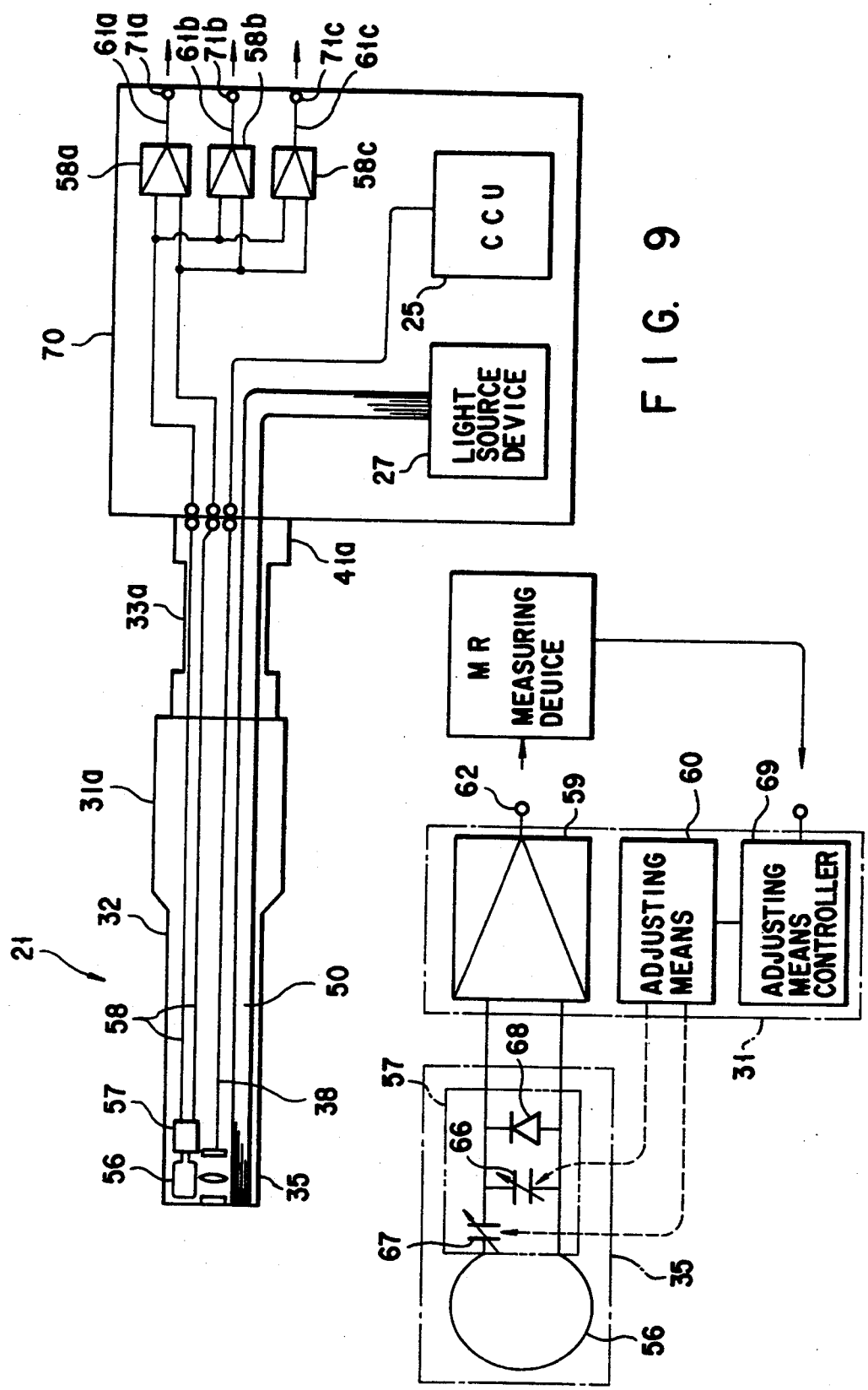
FIG. 8 is a schematic view showing a modification of the endoscope of FIGS. 6 and 7.
FIG. 9 is a view of an endoscope of the other modification similar to FIG. 6.

FIG. 8 shows a modification of the diagnostic system of FIGS. 6 and 7. The following will explain the portions, which are different from those of FIGS. 6 and 7.

According to this modification, adjusting means controller 69, which detects a signal sent from the MR measuring device 22, and automatically adjusts adjusting means 39, is provided in the handy controller 31 of the MR endoscope 21.

By the above structure, the MR signal, which is received by the loop antenna 56, is sent to the MR measuring device 22 through the matching circuit 57 and the pre-amplifier 59. Then, the adjusting means controller 69 can control adjusting means 60 by the feedback from the MR measuring device 22. The adjusting means controller 69 controls the variable capacitors 66 and 67 of the matching circuit 57, and automatically measures the suitable adjustment between the MR measuring device 22 and the MR endoscope 21.

In addition to the technical advantage explained in the embodiment of FIGS. 6 and 7, the endoscope of FIG. 8 has a technical advantage in that operability can be improved since the automatic adjustment of the matching circuit is made without adjusting the matching circuit to the type of the MR measuring device to be connected.

FIG. 9 shows another modification of the diagnostic system.

A universal cord 33a, which has the light guide 50, the image device signal line 38, and the MR signal line 58, is provided to be extended from the handy controller 31a. In other words, according to this modification, the universal cord 33a is formed by combining various types of cables and cords to one line. A connector 41a is provided at the end portion of the universal cord 33a to be connected to a unit-shape controller 70. The controller 70 comprises the light source device 27 and the CCU 25, and a plurality of pre-amplifiers 58a, 58b, 58c ... which are connected to each other in parallel. The MR signal line 58 is connected to the pre-amplifiers 58a, 58b, and 58c, which are formed in parallel. The signal lines 61a, 61b, and 61c are respectively extended from the pre-amplifiers, and are connected to connection terminals 71a, 71b, and 71c, which are connected to the outer unit of the controller 70. These connection terminals are connected to the MR measuring device as shown in FIG. 6. For example, the connection terminal 71a is a terminal for a predetermined MR measuring device, the connection terminal 71b is a terminal for the other MR measuring device, and the connection terminal 71c is a terminal for further other MR measuring device. The necessary types of the preamplifiers, signal lines, and connection terminals can be provided in accordance with the type of the MR measuring device to be connected.

According to the embodiment of FIG. 9, by providing the plurality of preamplifiers 58a, 58b, and 58c, the MR endoscope 21 can be selectively connected to various types of MR measuring devices having various circuit characteristics. The terminal may be selectively connected to the MR measuring device when connecting, and no adjustment is needed in accordance with the MR measuring device. Moreover, since the universal cord 33a is formed as one line, the connection can be easily made, and time for connection can be reduced.

FIGS. 10 to 15 show various types of peripheral units to be used in the nuclear magnetic resonance image apparatus in the diagnostic system using the nuclear magnetic resonance phenomenon.

According to the diagnostic system using the nuclear magnetic phenomenon, the MR antenna is provided at the endoscope or the top end portion of the probe, thereby obtaining a fine and accurate image having a good S/N ratio and being effective to diagnose the depths of the disease of the tubular viscus.

However, in operating the probe or the endoscope, the peripheral units such as a light source device and a suction device are needed, and these peripheral units are inevitably used in the vicinity of the MRI apparatus in order to obtain the fine image having a good S/N ratio. In the case that the peripheral units are used in the vicinity of the MRI apparatus, the peripheral units are put under the strong static magnetic field, which the magnet of the MRI apparatus generates. At this time, there is a possibility that the electromagnetic parts, which are provided in the peripheral units, will not normally operate because of the influence of the strong static magnetic field.

According to the diagnostic system of FIGS. 10 to 15, the parts whose operations are influenced by magnetism are arranged in such a direction where influence of magnetism, which is generated by the nuclear magnetic resonance image apparatus, is reduced. Thereby, the various types of peripheral units can be surely and normally operated without receiving influence of the strong static magnetic field, which the magnet of the nuclear magnetic resonance image apparatus generates.

Figure 10:
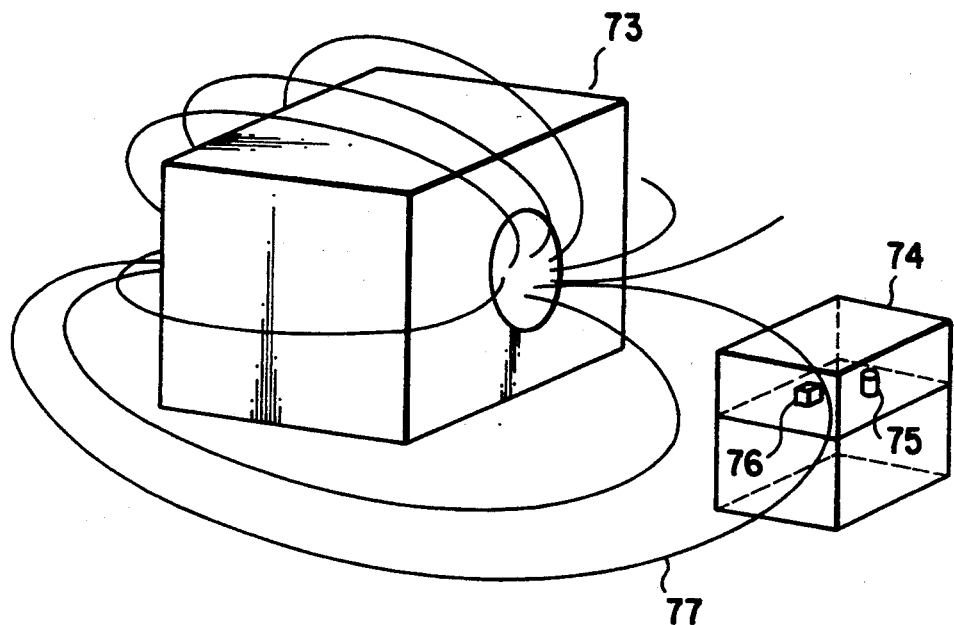
FIG. 10 is a schematic view showing a static magnetic field in the diagnostic system.
Figure 11:
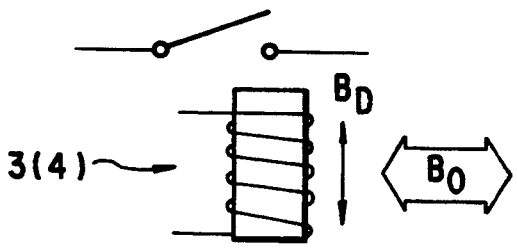
FIG. 11 is an explanatory view showing a direction where electromagnetic parts are provided in the static magnetic field.

According to the diagnostic system of FIGS. 10 and 11, the peripheral unit such as a light source device 74, which is necessary for the examination by the endoscope, is provided in the vicinity of a magnet 73 of the MRI apparatus. In the light source device 74, the electromagnetic parts, which receive influence of the magnetic field, such as a solenoid 75 and a relay 76 are provided. Moreover, a line of magnetic force (magnetic flux) 77 of the strong static electric field, which the magnet 73 generates, is leaked into the light source device 74.

As shown in FIG. 11, the electromagnetic parts, e.g., solenoid 75 and relay 76, provided in the light source device 74, are arranged in a state that a direction $B_D$ of the magnetic field, which is generated when each part operates, is placed at a position, which is perpendicular to a direction $B_O$ of the static magnetic field, which the magnet 73 of the MRI apparatus generates.

According to the above-mentioned structure in which the electromagnetic parts are provided in the peripheral units, the magnetic flux 77 of the strong static electric field, which the magnet 73 generates, is leaked into the housing of the the light source device 74 as a leakage magnetic flux. However, in the case of the operation of the electromagnetic part, which is influenced by the outer magnetic flux, the direction of magnetic flux, which the electromagnetic part generates, is set to be perpendicular to the outer magnetic flux, that is, leakage magnetic flux. Due to this, the electromagnetic part can be normally operated even under the environment in which the leakage magnetic flux sent from the outer unit exists. In other words, the operational direction of the solenoid 75 and the contact point opening/closing closing direction of the relay 76 are orthogonal to the direction of the leakage magnetic flux.

Therefore, according to the structure of the above embodiment, in a case that diagnosis and treatment are performed by other means under the strong magnetic field generated by the magnet 73 of the MRI apparatus, no influence is exerted on the operation of the electromagnetic part provided in the peripheral unit and the operation of the part, which is influenced by the magnetic field, even if the various types of peripheral units, which are necessary for the diagnosis using the endoscope, such as the light source device 74 and the suction device are provided in the vicinity of the magnet 73. Due to this, various types of peripheral units can be normally operated under the strong magnetic field.

Figure 12:
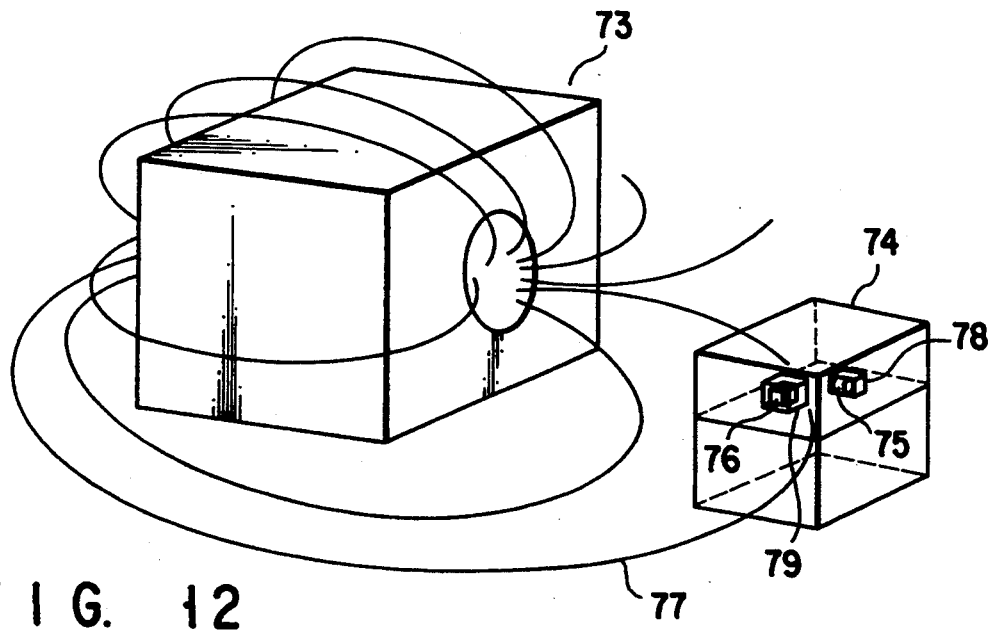
FIG. 12 is an explanatory view schematically showing a direction where the MRI apparatus is provided.

According to the arrangement of FIG. 12, the magnetic electronic parts, which are provided in the light source device 74 and which are influenced by the magnetic field, e.g., solenoid 75 and relay 76, are contained in magnet shielding boxes 78 and 79 formed of, for example, electromagnetic steel, respectively.

According to the structure of the above embodiment, even if the strong magnetic flux, which the magnet 73 of the MRI apparatus generates, is leaked into the housing of the light source device 74, the respective electromagnetic parts are shielded from being magnetized by the magnet shielding boxes 78 and 79 formed of the electromagnetic steel. Since the electromagnetic steel has high magnetic permeability and low coercive force, a sufficient magnetic shielding function can be obtained even under the strong magnetic field, which the magnet 73 of the MRI apparatus generates.

According to the above embodiment, even if the direction of the magnetic flux, which the electromagnetic parts generate, is set to be orthogonal to the outer magnetic flux, that is, leakage magnetic flux, when the electromagnetic parts of FIG. 10 are operated, the electromagnetic parts are shielded from being magnetized by the magnet shielding boxes, so that the leakage magnetic flux can be further reduced, and even a part, which is sensitive to the magnet, can be normally operated.

Therefore, the problem of the magnetic field, which cannot be solved by only the mounting direction of the parts, can be solved. Moreover, even if the parts cannot be arranged in the direction that the problem of the magnetic field is reduced by the limitation of the arrangement of the parts in the housing, the normal operation of the parts can be obtained by the shielding effect. In other words, the various types of the peripheral units can be normally operated even under the strong magnetic field.

Figure 13:
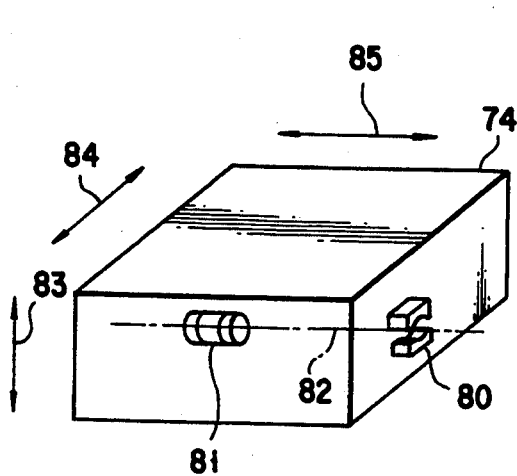
FIG. 13 is a perspective view showing a state wherein a light source device for the endoscope is provided in the static magnetic field.
Figure 14:
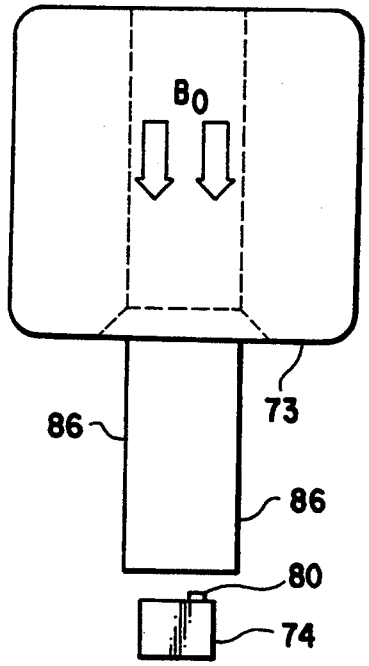
FIG. 14 is an explanatory view showing a state wherein a light source device is provided in the vicinity of a magnet of the MRI apparatus.
Figure 15:
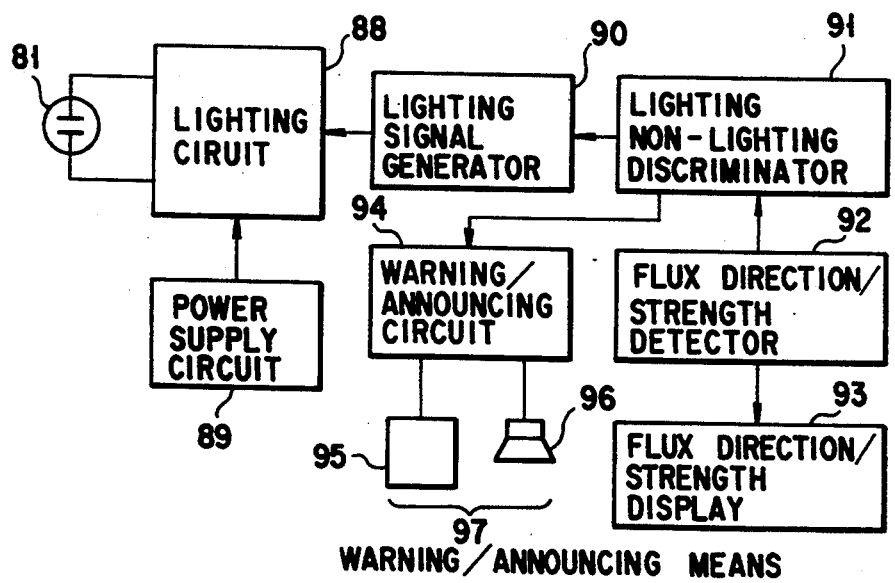
FIG. 15 is a block diagram schematically showing the structure of the light source device for the endoscope.

FIGS. 13 to 15 show the schematic structure of the light source device 74 for the endoscope. When the light source device 74 for the endoscope is used in the vicinity of the magnet 77 of the MRI apparatus, a discharge lamp 81, which is built into the light source device 74, is largely influenced by the static magnetic field. The discharge lamp 81 generates an arc discharge between the electrodes (not shown) and the discharge arc easily receives the influence of the magnetic field, and the arc is distorted in the magnetic field.

Therefore, by depending on a relative direction between the magnetic field, which is generated by the magnet 73 of the MRI apparatus and an optical axis 82, which connects a connector 80, which corresponds to an injection inlet of the light source device 74, to the discharge lamp 81, the discharge lamp 81 is not turned on, or the discharge lamp 81 is turned on as the arc of the discharge lamp 81 is distorted. Due to this, the outer temperature of the lamp 81 increases, and the lamp 81 may be broken.

The relative direction between the optical axis 82 of the discharge lamp 81 and the magnetic field is largely divided into three. More specifically, if the direction of the magnetic field, which is generated by the magnet, is set as shown by an arrow 83 or an arrow 84 in the figure, the discharge arc of the discharge lamp 81 is distorted, and the above-mentioned disadvantages occur. On the other hand, if the direction of the magnetic field, which is generated b the magnet 73, is set as shown by an arrow 85, the lamp can be normally turned on under the strong magnetic field since the discharge arc is not distributed in upper and lower directions to right and left directions between the electrodes. Therefore, if the direction of the optical axis 82 of the discharge lamp 81 is consistent with the direction of the magnetic field, the discharge lamp can be normally turned on under even strong magnetic field.

FIG. 14 is one example showing the direction of the arrangement of the light source device 74 in the vicinity of the magnet 73 of the MRI apparatus in view of the above-mentioned characteristic. In order to make the direction of the magnetic field and that of the light axis 82 of the discharge lamp 81 parallel to each other, the axis of the magnet 73 is set to be orthogonal or perpendicular to the front panel of the light source device 74 to the rear panel. In FIG. 14, the light source device 74 is arranged before a bed 86 connected to the magnet 73. However, in consideration of the direction of the magnetic flux and that of the light source device 74, it is possible to arrange the light source device 74 at the position other than the position shown in the figure.

FIG. 15 is a block diagram showing the schematic structure of the light source device 74. More specifically, a lighting circuit 88 for lighting the discharge lamp 81 is connected to a power source circuit 89 for generating a lighting signal and a lighting signal generator 90, and controlled by a signal sent from a lighting/non-lighting discriminator 91. In the vicinity of the discharge lamp 81, a single or a plurality of magnetic flux detector, e.g., a flux direction/strength detector 92 including a hole element and/or a Wiegand wire is provided. The lighting/non-lighting discriminator 91 and a flux direction/strength display 93 are connected to the flux direction/strength detector 92. The lighting/non-lighting discriminator 91 is connected to a warning/announcing circuit 94 in addition to the lighting signal generator 90. Moreover, a warning/announcing means 97 for warning/announcing by light and sound generated by a warning lamp 95 and a warning speaker 96 is connected to the warning/announcing circuit 94.

Therefore, the magnetic flux close to the discharge lamp 81 is divided into the strength of each directional component, and detected by the flux direction/strength detector 92. The detection signal is inputted to the flux direction/strength display 93, the strength of the magnetic flux of each direction is converted to density of magnetic flux and displayed, or the direction of the magnetic flux close to the lamp is displayed.

One output signal of the flux direction/strength detector 92 is inputted to the lighting/non-lighting discriminator 91. The lighting/non-lighting discriminator 91 discriminates whether or not the magnetic field close to the discharge lamp 81 generates lighting defectiveness of the lamp. If it is discriminated that no lighting defectiveness is generated, a light allowing signal is inputted to the lighting signal generator 90, and a lighting signal is generated, and inputted to the lighting circuit. Then, based on this signal, the lighting circuit 88 turns on the discharge lamp 81.

If it is discriminated that no lighting defectiveness of the discharge lamp 81 is generated by the lighting/non-lighting discriminator 91, a light prohibiting signal is inputted to the lighting signal generator 90, and no lighting signal is generated, and the start of the lighting of the discharge lamp 38 is not performed. At the same time, the light prohibiting signal is outputted to the warning/announcing circuit 94. Since strength of the magnetic field close to the lamp is high and lighting defectiveness is generated, the warning/announcing circuit 94 announces that the light source device 74 is in a light prohibiting state, and warns that the strength of the magnetic field, which has influence upon the lighting, is high.

In the light source device 74, there is provided a protection function, which determines whether or not the magnetic flux, which passes through the discharge lamp 81, influences the lamp lighting state, and which allows the lighting of the discharge lamp 81 only in the case that the light source device 74 is arranged in the direction that no lighting defectiveness occurs.

Therefore, in the case that it is announced that the discharge lamp 81 cannot be lightened, the direction 10 and position of the light source device 74 are adjusted again with reference to the strength of the magnetic field displayed on the display, thereby making it possible to obtain the light allowing state. Due to this, it is possible to safely and surely perform the examination using the endoscope.

As explained above, the parts of the respective peripheral units whose operations are influenced by magnetism are arranged in such a direction that the influence of magnetism, which is generated by the nuclear magnetic resonance image apparatus, is reduced. Thereby, the various types of peripheral units, which are arranged close to the magnet of the nuclear magnetic resonance image apparatus, can be surely and normally operated even under the strong magnetic field, and safety of the patient, who is examined and treated, can be ensured.

If the above-mentioned technical advantage can be obtained by the above-mentioned diagnostic system using the nuclear magnetic resonance phenomenon, there must be satisfied the need for performing the fine and accurate image diagnosis and examination of tissue of the living body to surely perform the diagnosis or the needs for performing the treatment against the portion of the disease, which is recognized by the image diagnosis, under the examination by the endoscope.

However, the conventional treatment implement for the endoscope is normally formed of magnetic material. Due to this, if the treatment implement is inserted into the patient in the MRI apparatus, the treatment implement is attracted by the extremely strong static magnetic field of the magnet of the MRI apparatus, and danger is exerted on the patient. Moreover, the magnetic field is largely disturbed by magnetism of the treatment implement, and the MR image is largely distorted, so that image-diagnosis cannot be performed.

Figure 16:
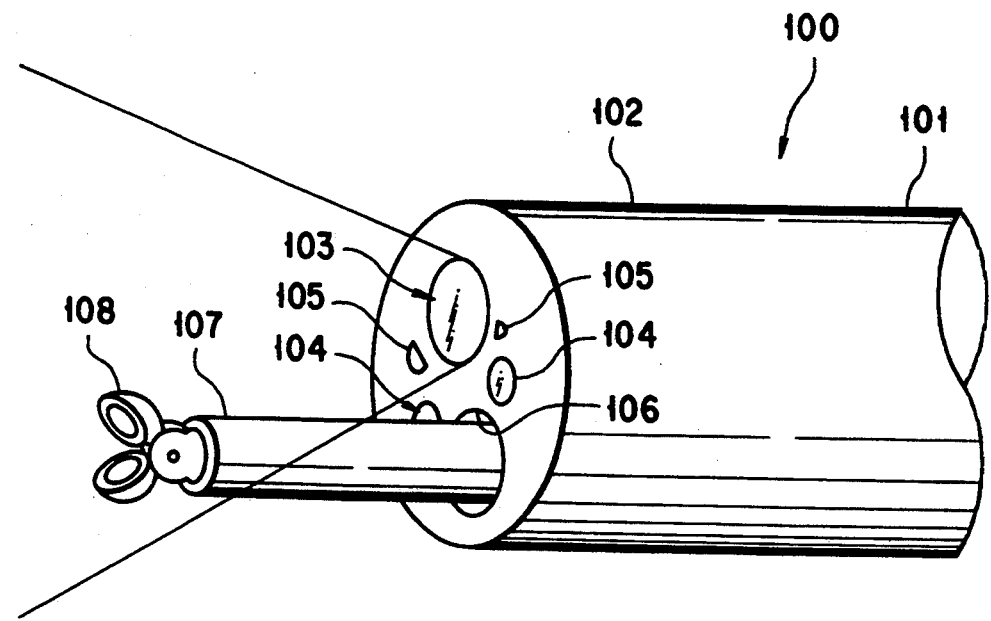
FIG. 16 is a schematic perspective view showing a top end portion of the endoscope.

FIG. 16 shows a top end side of an insertion section 101 of an endoscope 100 when an examination and treatment are performed by use of a treatment implement for endoscope under the examination by an endoscope. Reference numeral 102 is a top end portion provided in the insertion section 101 of the endoscope 100, and an observation optical system 103, an illumination optical system 104, an injection nozzle 105, and a channel 106 for treatment implement are provided thereon. An implement 107 is inserted to the channel 106 and is projected from the top end portion 102, and treatment is performed within the endoscope observation field of vision by use of forceps.

Figure 17:
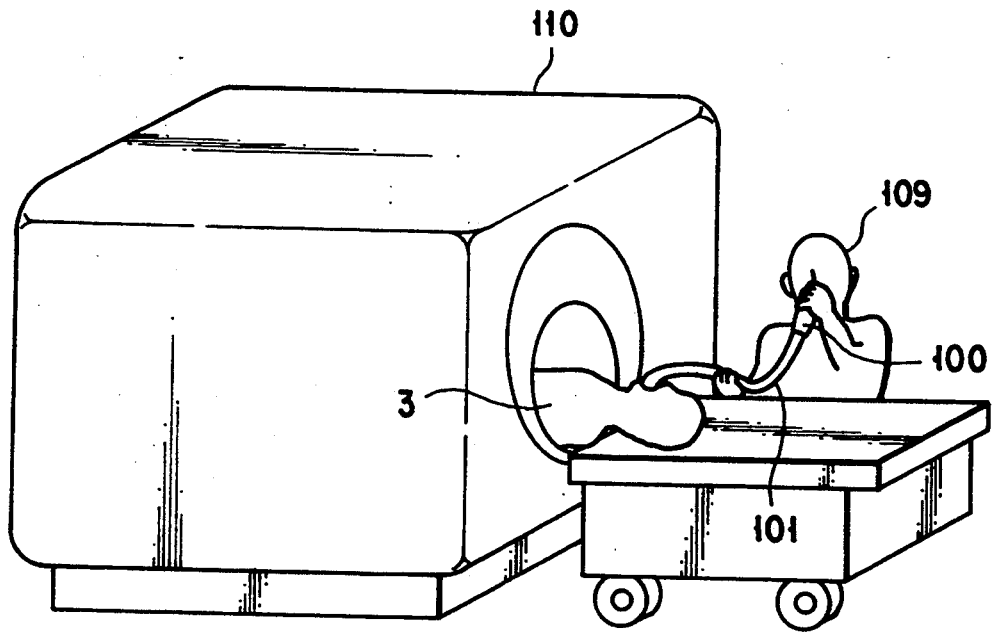
FIG. 17 is a perspective view showing a state that the MRI apparatus is used.

FIG. 17 shows a state that a medical expert inserts the insertion section 101 of the endoscope 100 into the patient 3 on an MRI apparatus 110, and examines the living body of the patient. The endoscope 100 is formed of non-magnetic material in order to be used in the strong magnetic field of the MRI apparatus 110. Moreover, on the top end portion of the insertion section 101 of the endoscope 100, there is formed a high frequency coil for receiving an MR signal from a disease portion (FIG. 3 and FIGS. 6 to 9), and the medical expert can MR-image-diagnose the disease portion while observing it through the endoscope.

FIGS. 18A to 18L show a top end portion of each of various types of treatment implements for endoscope.

Figure 18A:
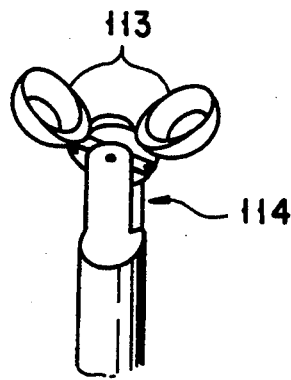
FIGS. 18A to 18L are schematic perspective views showing various types of treatment implements for the endoscope.
Figure 18B:
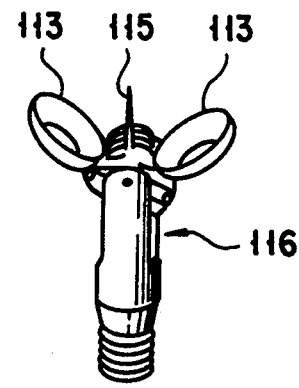
Figure 18C:
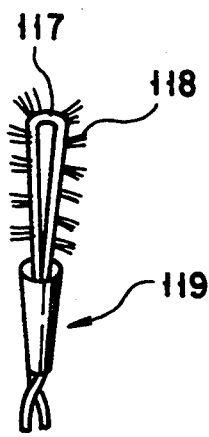
Figure 18D:
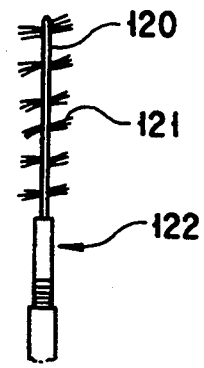

FIG. 18A shows a forceps 114 having a pair of cups 113, which are freely opened and closed. FIG. 18B shows a forceps 116 having the pair of cups 113 and a needle 115. FIG. 18C shows a brush 119 for examining tissue, which is formed by putting a brush hair 118 on an inverse-U shaped wire 117. FIG. 18D shows a brush 122 for examining tissue, which is formed by putting a brush hair 121 on a rod-shape wire 120.

Figure 18E:
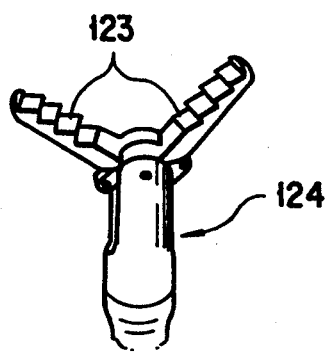
Figure 18F:
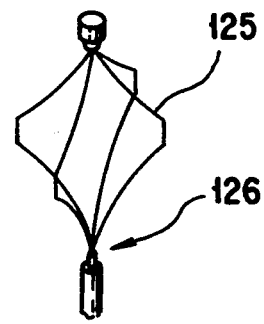
Figure 18G:
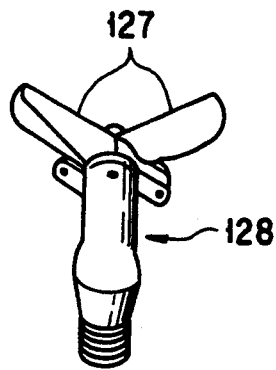
Figure 18H:
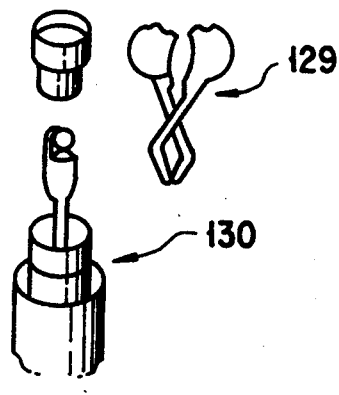

FIG. 18E shows a crocodile holding forceps 124 having a forceps 123, which is freely opened and closed. FIG. 18F is a basket type holding forceps 126 having a basket 125. FIG. 18G shows a scissors forceps 128 having a pair of scissors 127. FIG. 18H is a clip device 130 having a clip 129.

Figure 18I:
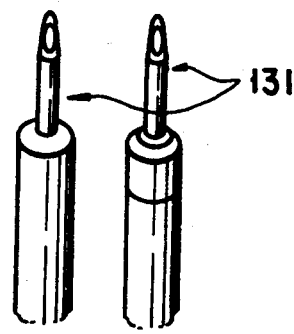
Figure 18J:
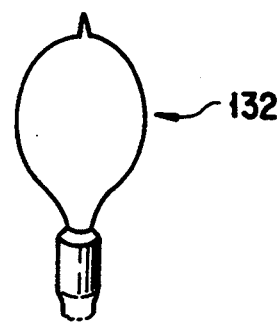
Figure 18K:
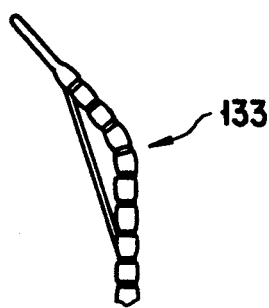
Figure 18L:
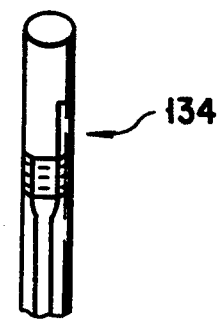

FIG. 18I shows an injection needle 131. FIG. 18J shows an elliptical high frequency snare 132 for an electrical scalpel. FIG. 18K is a snare (papillotomy knife) 133 for an electrical scalpel to cut a duodenum and a papilla. FIG. 18L shows a heat probe 134.

Each of the above implements including the handy control section, insertion section, and top end mechanism, is formed of non-magnetic material. For example, plastic is used as the handy control section, a resin-made tube is used as a sheath, a non-magnetic metal such as phosphor bronze is used as a coil sheath, a tungsten wire is used as a wire, a titanium alloy is used as a top end portion, and copper or brass is used as other metallic parts, and a constant voltage diode is used as a heat element as shown in FIG. 18L.

According to the above-structured treatment implement for the endoscope, the treatment implement is not attracted even in the strong magnetic field of the magnet of the MRI apparatus 110 (FIG. 17). Therefore, the disease portion can be examined by the endoscope 100, the MR diagnostic image of the disease portion can be formed, necessary treatments, examination of living body, and examination of tissue can be performed immediately under the examination by the endoscope.

In other words, according to the above-structured treatment implement for the endoscope, since the treatment implement is formed of non-magnetic material, the treatment implement is not attracted by the extremely strong magnetic field of the magnet of the MRI apparatus 110 even if it is inserted into the patient 3 in the MRI apparatus 110, and no danger may be exerted on the patient 3.

Since the treatment implement is non-magnetic, the magnetic field is not disturbed, and the MR image is not distorted, so that there can be obtained the technical advantage in which both fine and accurate image-diagnosis and the treatment using the endoscope can be performed.

FIGS. 18A to 18L show only a part of the examples of the treatment implements. If the other treatment implements are formed of non-magnetic material similar to the above embodiment, exactly the same technical advantage can be obtained. Therefore, the present invention is not limited to the treatment implements shown in the embodiment.

In the above-mentioned diagnostic system, the insertion section, which has the flexible thin tube of the endoscope, is formed of non-magnetic material in order not to be attracted by the strong magnetic field of the magnet of the MRI apparatus and not to distort the MR image by disturbing the magnetic field.

However, in the insertion section having the flexible thin tube such as the endoscope, it is difficult to structure a curved control section controlling a curved portion and a handy control section having an eye-piece by the non-magnetic member in view of processing and cost. To solve this problem, it is considered that the entire effective length of the insertion section is made longer so as not to be influenced by the magnetic field of the magnet, and the handy control section is arranged further away from the magnet.

In the actual use, the top end portion of the insertion section is inserted into the patient, and the scanning is performed by the MRI apparatus in a state that the handy control section is away from the magnet. However, the control section may be attracted by the magnetic field of the magnet during the scanning, and there may occur the danger that the control section will collide with the patient.

Figure 19:
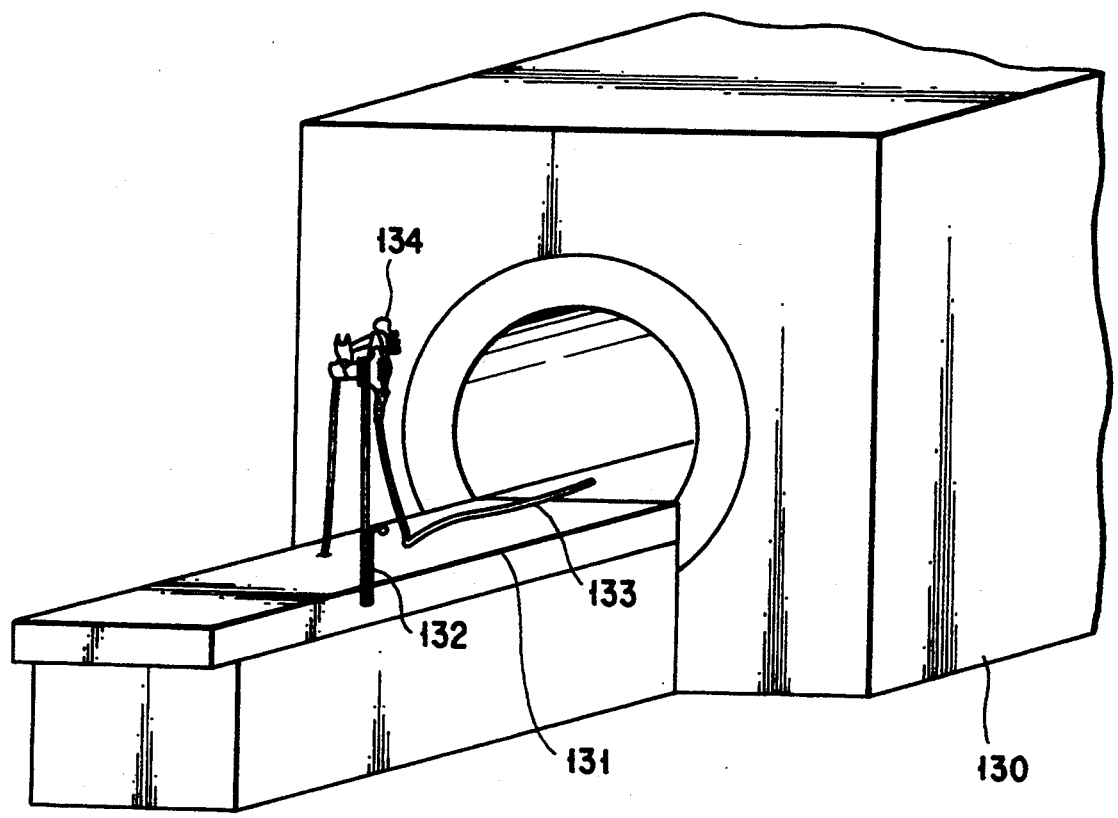
FIG. 19 is a schematic perspective view showing the MRI apparatus having a hanger for the endoscope.

FIG. 19 shows a hanger 132 for the endoscope, which is provided on a bed 131 of the MRI apparatus 130, and which holds a control section 134 of an endoscope 133.

Figure 20:
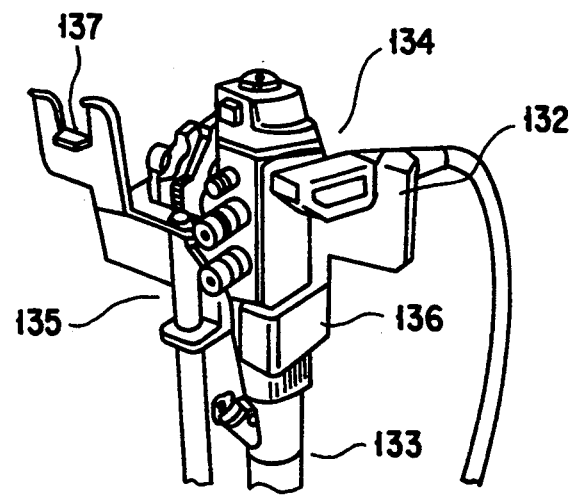
FIG. 20 is a perspective view showing the hanger for the endoscope.

FIG. 20 shows a state that a holding section 135 of the hanger 132 holds the control section 134. A hung section 136 and a switch 137 are provided in the holding section 135.

The hung section 136 is directed to hold the control section 134 in order not to prevent the control section section 134 from being attracted by magnetic force of the magnet. The switch 137 is provided to be turned on by the control section 134 when the control section 134 is correctly held by the holding section 135. The switch 137 is connected to allowing means (not shown) of the MRI apparatus 130.

In other words, the control section 134 of the endoscope 133, which is inserted into the patient, is held by the holding section 135 of the hanger 132 when the scanning is performed by the MRI apparatus 130. At this time, if the control section 134 is correctly held and protected from being attracted by the magnetic force of the magnet, allowing means of the MRI apparatus 130 allows the MRI apparatus to scan. That is, the MRI apparatus 130 can scan only when the control section 134 of the endoscope 133 is held in a predetermined safe state.

Moreover, since the control section 134 of the endoscope 133, which is formed of the non-magnetic member, is not attracted by the magnet when the scanning is performed by the MRI apparatus 130, safety for the patient can be extremely improved. Therefore, there can be obtained a technical advantage in which the safety for the patient can be ensured without increasing the manufacturing cost of the endoscope 133.

Figure 21:
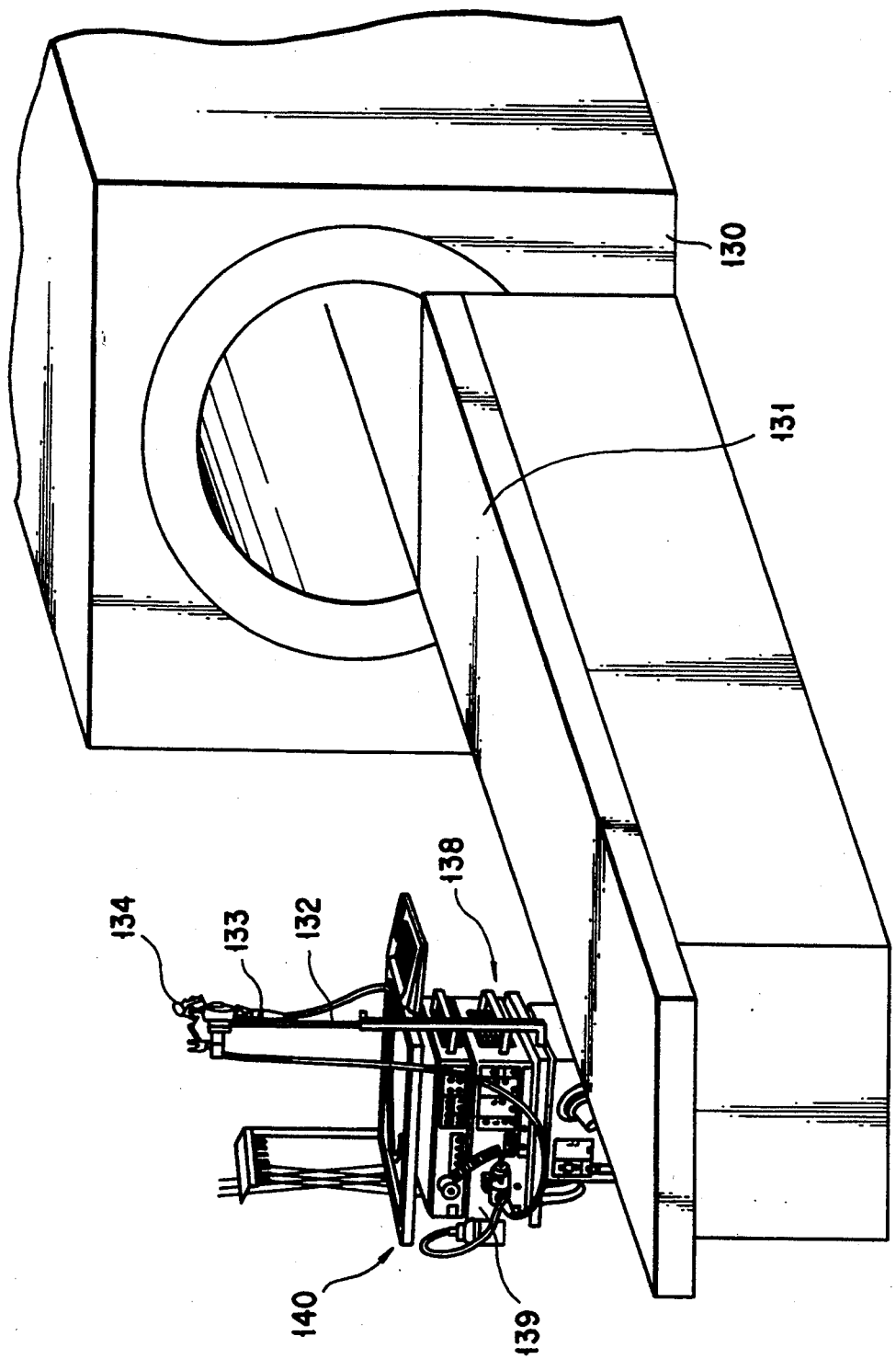
FIG. 21 is a schematic perspective view showing the MRI apparatus having a trolley for the endoscope.

In addition, the same technical advantage can be also obtained by providing the hanger 132 on a trolley 138 for the endoscope, which is formed of non-magnetic material, as shown in FIG. 21, without providing it in the bed 131 of the MRI apparatus 130. Moreover, there can be obtained a technical advantage in which a light source device 139 for the endoscope and a peripheral unit 140 can be contained in the trolley 138, in addition to the prevention of the attraction of the control section 134.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A diagnostic system using a nuclear magnetic resonance phenomenon, comprising:
   an external magnetic field generator, provided externally of a living body, for generating a magnetic field in a living body;
   a thin diameter member which is insertable into a body cavity of the living body, and said thin diameter member having flexibility;
   a high frequency coil, provided at a top end of said thin diameter member, for transmitting and receiving a high frequency signal;
   a nuclear magnetic resonance signal measuring device for receiving a nuclear magnetic resonance signal from the living body; and
   isolating and separating means, provided between said high frequency coil and said nuclear magnetic resonance signal measuring device, for electrically isolating and separating said high frequency coil from said nuclear magnetic resonance signal measuring device in a manner such that the nuclear magnetic resonance signal is transmittable between said high frequency coil and said nuclear magnetic resonance signal measuring device.

2. The system according to claim 1, further comprising amplifying means for amplifying the high frequency signal received by said high frequency coil.

3. The system according to claim 2, wherein said isolating and separating means comprises a high frequency transducer having:
   a first wire connected to said nuclear magnetic resonance signal measuring device, and
   a second wire connected to an output side of said amplifying means and electrically insulated from said first wire.

4. The system according to claim 3, further comprising a stabilizing d.c. power source connected to supply a d.c. bias voltage to said amplifying means.

5. The system according to claim 2, wherein:
   said amplifying means comprises a pre-amplifier; and
   said isolating and separating means comprises an isolation amplifier provided between said pre-amplifier and said nuclear magnetic resonance signal measuring device.

6. The system according to claim 5, further comprising a stabilizing d.c. power source for supplying a d.c. bias voltage to said pre-amplifier and to said isolation amplifier.

7. The system according to claim 1, wherein said thin diameter member comprises an endoscope.

8. A diagnostic system using a nuclear magnetic resonance phenomenon, comprising:
   a control section provided internally of the diagnostic system;
   an insertion section of thin diameter, extending from said control section, and being insertable into a body cavity of a living body, and said insertion section having flexibility;
   an endoscope having a high frequency antenna provided in said insertion section;
   a plurality of magnetic resonance signal measuring devices for processing a nuclear magnetic resonance signal from said high frequency antenna; and
   matching means for selectively coupling said high frequency antenna to each of said plurality of magnetic resonance signal measuring devices having a different circuit impedance characteristic.

9. The system according to claim 8, wherein said antenna is a loop antenna, and said matching means includes:
   a first variable capacitor connected to said antenna in parallel, and
   a second variable capacitor connected to said antenna in series, and
   wherein said matching means is arranged to impedance-match said antenna and each of said magnetic resonance signal measuring devices.

10. The system according to claim 9, wherein said matching means further includes a diode arranged in parallel to said loop antenna.

11. The system according to claim 9, wherein said control section includes adjusting means provided in said control section for adjusting a capacity of each of said variable capacitors.

12. The system according to claim 11, wherein each magnetic resonance signal measuring device forms a signal showing a matching state between said matching means and each magnetic resonance signal measuring device when receiving each magnetic resonance signal from said antenna through said matching means.

13. The system according to claim 12, further comprising a controlling device coupled to receive said signal showing the matching state, and to actuate said adjusting means based on said received signal.

14. The system according to claim 8, wherein said matching means is connected to said antenna, and comprises a plurality of pre-amplifiers, each pre-amplifier having a different circuit impedance characteristic, and wherein each of said pre-amplifiers is connectable to each of said magnetic resonance signal measuring devices having a corresponding circuit impedance characteristic.

15. The system according to claim 14, wherein said endoscope comprises:
   a universal cord extending from the control section, and
   a signal line passage extending to the universal cord from said antenna.

16. The system according to claim 15, wherein said endoscope further comprises:
   a light guide, contained in the insertion section, for providing an illumination light to a portion of an object to be examined from an end surface of the insertion section; and
   an objective optical system optically coupled to said light guide for receiving light reflected from the portion of the object to be examined, and
   wherein said light guide extends to said universal cord from the insertion section.

17. The system according to claim 16, wherein said endoscope further comprises:
   an image-forming device, contained in the insertion section, for converting an image corresponding to the light received by said objective optical system to an electrical signal; and
   a signal line passage having an end connected to said image-forming device, and extending to an inside portion between said insertion section and said universal cord.

* * * * *